United States Patent [19]
Takase

[11] Patent Number: 5,254,082
[45] Date of Patent: Oct. 19, 1993

[54] ULTRASONIC SURGICAL SCALPEL

[76] Inventor: Haruo Takase, 20-16, Shimoochiai 3-chome, Shinjuku-ku Tokyo, Japan

[21] Appl. No.: 682,896

[22] Filed: Apr. 9, 1991

Related U.S. Application Data

[63] Continuation of Ser. No. 481,163, Feb. 20, 1990, abandoned.

[30] Foreign Application Priority Data

Feb. 18, 1989 [JP] Japan ............................ 1-18167[U]

[51] Int. Cl.$^5$ ............................................ A61B 17/20
[52] U.S. Cl. .................................... 604/22; 604/119; 606/107
[58] Field of Search .................. 128/24; 604/22, 118, 604/119; 606/107

[56] References Cited

U.S. PATENT DOCUMENTS

| | | | |
|---|---|---|---|
| 3,589,363 | 6/1971 | Banko et al. | 604/22 |
| 3,945,375 | 3/1976 | Banko | 604/22 |
| 3,974,833 | 8/1976 | Durden | 604/119 |
| 4,246,902 | 1/1981 | Martinez | 604/22 |
| 4,428,748 | 1/1984 | Peyman et al. | 604/22 |
| 4,750,902 | 6/1988 | Wuchinich et al. | 128/24 AA |
| 4,886,060 | 12/1989 | Wiksell | 604/22 |

*Primary Examiner*—David M. Shay
*Attorney, Agent, or Firm*—Oblon, Spivak, McClelland, Maier & Neustadt

[57] ABSTRACT

An ultrasonic surgical scalpel comprising a suction nozzle having a suction mouth which is open aside toward the direction different from that of the axis of the nozzle, and a suction regulating mouth formed in a suction pipe extending from the suction nozzle so as to communicate with a suction passage inside the suction nozzle. The suction mouth being open aside allows the leading end of the nozzle to be mad acute or round, thereby to enable the suction nozzle to be readily inserted and moved in subcutaneous or organic tissues while shattering the tissues with ultrasonic vibrations. When sucking out the tissues shattered with the vibrations, by selectively opening and closing the suction regulating mouth with a finger tip, sucking force for sucking out the tissues can be freely controlled with ease.

7 Claims, 2 Drawing Sheets

ULTRASONIC SURGICAL SCALPEL

This application is a continuation of application Ser. No. 07/481,163, filed on Feb. 20, 1990, now abandoned.

BACKGROUND OF THE INVENTION

1. Field of the Invention

This invention relates to an ultrasonic surgical scalpel capable of effectively shattering subcutaneous or organic tissues of a living body into its mushy state by use of ultrasonic vibrations and sucking out the shattered tissues by use of sucking force.

2. Description of the Prior Art

There has been well known an ultrasonic surgical scalpel for use in a plastic surgical operation to remove subcutaneous adipose tissues or an organic surgery to remove liver or other organic tissues and so on, which comprises an ultrasonic vibrator incorporated in a handpiece and a hollow horn connected to the vibrator Vibrations generated by the vibrator are magnified in amplitude in a matter of two times to several ten times when propagating from the basal end attached to the vibrator to the leading end of the horn.

When performing the plastic surgical operation to remove, for example, subcutaneous adipose tissues of a patient's body, the leading end of the aforesaid scalpel horn is inserted into under the skin of the patient's body, and then, the vibrator is driven to vibrate the horn so as to shatter the subcutaneous adipose tissues into its mushy state. While shattering the subcutaneous tissues with ultrasonic vibrations generated by the vibrator, sucking force is applied to inside the hollow horn to suck out the subcutaneous tissues shattered into the mushy state as noted above through a suction passage in the horn. Thus, the subcutaneous tissues can be shattered with the ultrasonic vibrations and removed out of the patient's body through the horn.

In the prior art ultrasonic scalpel, the hollow horn is used as a suction tube through which the shattered tissues or fat in the mushy state are sucked out and provided in its leading end with a suction mouth. In a general way, this suction mouth is open just frontward in the axial (lengthwise) direction of the horn. That is, the secant plane defining the mouth at the leading end of the horn perpendicularly intersects the axis of the horn. This conventional ultrasonic scalpel has however entailed a disadvantage that it produces relatively large resistance when being inserted into the subcutaneous or organic tissues so as to advance against the tissues with difficulty because the secant plane forming the mouth is perpendicular to the axis of the horn. This is one of the reasons why the surgical operation is difficult. Besides, forcible insertion of the horn into the subcutaneous or organic tissues causes blood vessels, nerve tissues and so on to be injured needlessly, consequently to elongate the period for healing an operation wound.

Particularly in a case of inserting the scalpel horn into between the skin and the subcutaneous tissue of the living body, the scalpel horn cannot be moved forward along the inner surface of the skin in a desired direction and is apt to advance into the subcutaneous tissue, because the suction mouth is open straight frontward in the axial direction of the horn.

Furthermore, the conventional ultrasonic scalpel is generally connected to an external aspirator in order to aspirate subcutaneous tissues shattered into its mushy state with ultrasonic vibrations. Generally, sucking force generated by the aspirator is adjusted by operating a suction adjusting means provided on the aspirator or a suction regulating valve mounted on the handpiece. Either way, the work becomes onerous where the adjusting means or regulating valve is frequently operated to control the sucking force to be given to inside the scalpel horn in the midst of a surgical operation. Also, the surgical scalpel with the latter suction regulating valve is complicated in structure and awkward.

OBJECT OF THE INVENTION

One object of this invention is to provide an ultrasonic surgical scalpel totally free from such defects of the conventional ultrasonic scalpels mentioned above, which can effectively shatter and suck out unnecessary subcutaneous or organic tissues to be removed without needlessly injuring other tissues such as blood vessels and nerve tissues in advancing the scalpel in under the tissues.

Another object of the invention is to provide an ultrasonic surgical scalpel having a suction regulating means which is simple in structure and can be readily operated with the finger tip of an operator.

SUMMARY OF THE INVENTION

To attain the objects described above according to this invention, there is provided an ultrasonic surgical scalpel comprising a vibrator contained within a handpiece and a horn connected to the vibrator and adapted to transmit vibrations generated by the vibrator to the leading end thereof and magnify the vibrations, wherein the aforementioned horn is provided with a suction passage and a suction mouth being open perpendicular to a direction different from the axial direction of the horn.

The aforementioned handpiece may preferably be provided with a suction regulating mouth communicating with the suction passage formed inside the horn.

According to this invention, the leading end can be formed acute or substantially round because the suction mouth need not to be formed so as to be open just frontward. That is, the suction mouth can be formed simply by diagonally cutting the leading end part of the horn or in the circumferential surface of the horn. As a result, the leading end of the horn may be formed aslant or round so as to enable the horn to be readily and smoothly inserted into under the skin, organic tissues or the like without needlessly injuring blood vessels, nerve tissues and so on.

With the suction regulating mouth formed in the handpiece so as to communicate with the suction passage inside the horn, sucking force which is generated by an external aspirator connected to the scalpel and given to inside the horn can be easily regulated with the finger tip of an operator as it is held with the operator's hand.

These and other objects and characteristics of the present invention will become apparent from the further disclosure to be made in the detailed description given below.

BRIEF DESCRIPTION OF THE DRAWINGS

The preferred embodiments of the present invention will now be explained in detail with reference to the accompanying drawings, wherein.

DESCRIPTION OF THE PREFERRED EMBODIMENTS

Figures 1, 2:
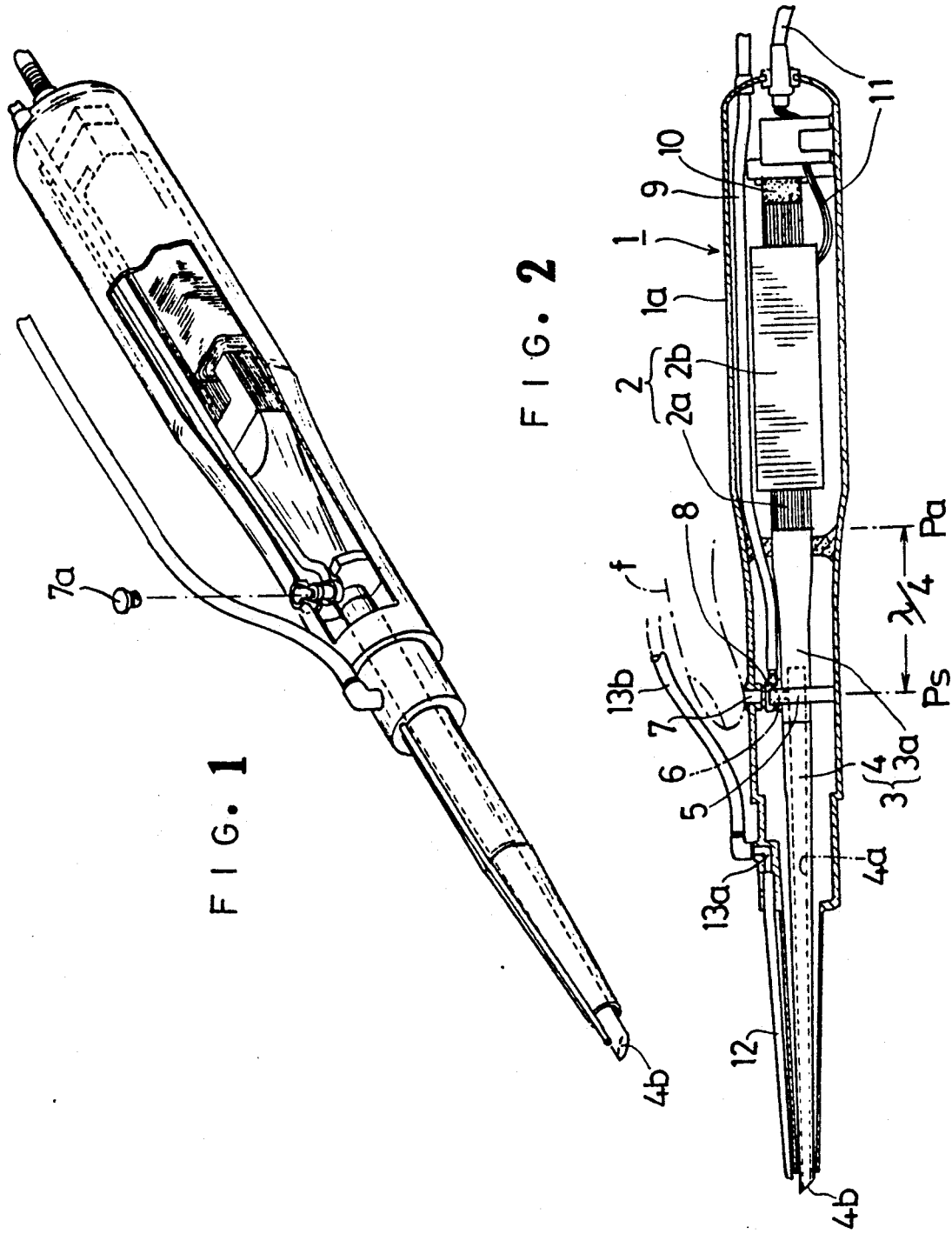
FIG. 1 is a partially section perspective view showing a first embodiment of the ultrasonic surgical scalpel according to this invention.
FIG. 2 is a side view in section showing the scalpel of FIG. 1.

The first preferred embodiment of the ultrasonic surgical scalpel according to this invention will be described with reference to FIGS. 1 and 2. In the drawings, reference numeral 1 denotes a handpiece and 1a a casing. The casing 1a accommodates an ultrasonic vibrator 2 and a horn 3 connected to the vibrator 2. The substantially front half part of the horn 3 serves as a suction nozzle 4 having a suction passage 4a bored along the axis of the horn. In this embodiment, the suction nozzle 4 is separately formed and detachably attached to the substantially rear half part (basal half) of the horn 3, but it may of course be incorporated with the basal half of the horn in one body.

The leading end part of the suction nozzle 4 somewhat protrudes forwards from the leading end of the casing 1. In the illustrated embodiment, the suction nozzle 4 is provided in the leading end part thereof with a suction mouth 4b.

The ultrasonic vibrator 2 is composed of a ferromagnetic core 2a and an electromagnetic coil 2b wound around the core 2a. By applying an alternating current to the coil 2b, electrostrictive vibrations are generated in the core 2a.

Otherwise, there may be used a magnetostrictive vibrator which generates vibrations by utilization of magnetostrictive phenomenon. However, the vibrator of this type is feeble in electromagnetic converting efficiency (about 30%), namely, about 70% of electric energy applied to the vibrator in the form of electricity is wasted in the form of heat. This implies the need of a cooling system for refluxing air or water around the vibrator. Therefore, if the magnetostrictive vibrator is employed in the ultrasonic scalpel, such a cooling system should be incorporated therein.

To be more specific, the electrostrictive vibrator used preferably in the scalpel of the invention has an outstanding advantage that it can generate vibrations with a high efficiency of about 90% or above, and further, stably produce an sufficient energy even when load applied thereto is fluctuated due to its high energy modulus. By this reason, the scalpel according to this invention employs the electrostrictive vibrator.

The horn 3 incorporating the suction nozzle 4 has a function of magnifying the amplitude of vibrations generated by the vibrator and effectively shattering the subcutaneous tissue of a living body into its mushy state with the vibrations transmitted to its leading end being brought into contact with the tissue. Thus, the horn 3 may preferably be made of metallic material having large endurance limit so as to sufficiently withstand vibrations having the increased amplitude (about 100 $\mu$m) of high frequency. As an example, a titanium alloy which is relatively small in metallic fatigue is suitable for the horn.

The horn 3 is supported by a supporting member 5 made of elastic material at a point (supporting point Ps) substantially one-fourth the wavelength of vibration $\lambda$ away from the connection point (Pa) at which the horn 3 and the vibrator 2 are connected, i.e. $\lambda/4$.

At the supporting point Ps, there is formed a connection port 6 communicating with the suction passage 4a formed inside the suction nozzle 4. To the connection port 6 is connected a suction regulating mouth 7 formed in the casing 1a of the handpiece 1 through the medium of a connection member 8. This connection member 8 is also connected to a suction pipe 9 which extends outside through the rear end of the casing 1a and is connected with an external aspirator (not shown).

In other words, the suction regulating mouth 7 is substantially formed in the course of the suction pipe 9 connected to the connection port 6 formed in the rear end part of the suction nozzle 4, namely, in the substantially central part of the horn, and may practically be formed in the casing 1a at a position based on human engineering so as to be readily opened and closed directly with the finger tip of an operator. In a case where the suction regulating mouth 7 need not be opened, it may be closed detachably with a lid member 7a.

Besides the requirement that the length from the supporting point Ps at which the supporting member 5 is disposed to the connection portion Pa should be substantially $\lambda/4$ as noted above, it is desirable that the length from the supporting point Ps to the leading end of the horn 3 (suction nozzle 4) be substantially three-fourth the wavelength of the vibration $\lambda$ generated by the vibrator 2, i.e. $3\lambda/4$. The length of the vibrator 2 should be substantially one-half the wavelength of the vibrator ($\lambda/2$).

Figure 3:
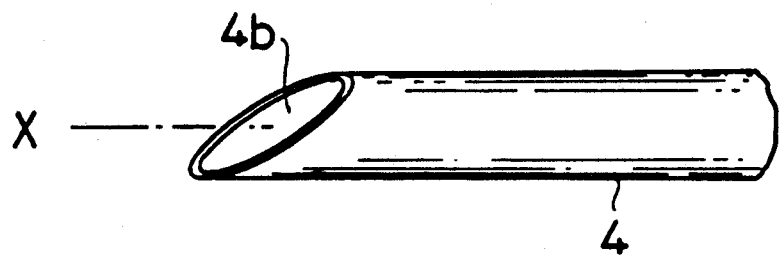
FIG. 3 is an enlarged side view of the leading end part of the same scalpel.

The suction mouth 4b formed at the leading end of the suction nozzle 4 is defined by cutting aslant the suction nozzle 4 at an angle of substantially 45° so as to direct toward the different direction from the axis X of the horn, as illustrated in FIG. 3.

In the drawings, reference numeral 10 denotes a retaining member of elastic material for fixing elastically the rear end of the vibrator 2 onto the casing 1a, and 11 an electric power cord for supplying an alternating current to the vibrator 2.

In the illustrated embodiment as noted above, along the outer surface of the suction nozzle 4, there is provided a flushing pipe 12 so as to supply Ringer's solution or other cleaning fluid to around the suction mouth 4b formed in the leading end of the suction nozzle 4. The flushing pipe 12 is detachably retained by a joint portion 13a formed on the casing 1a and connected with a conduit 13b through which the aforementioned cleaning fluid is fed to the flushing pipe 12.

The ultrasonic surgical scalpel having the aforenoted structure according to this invention can be appropriately applied to a plastic surgical operation to remove subcutaneous adipose tissues as an example in the following manner.

First of all, the leading end of the suction nozzle 4 is inserted into under the skin of a patient's body, and then, the vibrator 2 is actuated by being applied with an alternating current to vibrate the horn 3 so that the subcutaneous adipose tissues of the patient's body are shattered into its mushy state by vibrations which are generated by the vibrator 2 and amplified by the horn 3. Simultaneously, sucking force is applied to inside the horn 3 for sucking the shattered subcutaneous tissues in the suction passage 4a inside the suction nozzle 4.

When the subcutaneous tissues shattered into the mushy state are sucked out, the operator who holds the handpiece 1 in his hand can freely regulate the sucking force by directly opening or closing the suction regulating mouth 7 with his finger tip.

That is, when the suction regulating mouth 7 is completely closed with the finger tip, the sucking force generated by the aspirator is applied into the suction passage 4a in the suction nozzle 4 without loss, with the result that the internal pressure in the suction passage 4a becomes equal to the sucking force fed from the aspirator. Thus, the suction force at this time in the suction passage 4a becomes the largest. On the other hand, by selectively opening the suction regulating mouth 7 with the finger tip, the sucking force given into the suction passage 4a can be varied in proportion to the opening size of the suction regulating mouth 7. In this manner the sucking force suitable for sucking out the shattered tissues can be obtained any time.

By supplying the cleaning fluid such as Ringer's solution to around the suction mouth 4b through the flushing pipe 12 in performing a surgical operation, the shattered tissues can be effectively sucked out.

Also in this embodiment, the scalpel has the acute leading end, so that resistance produced when inserting the suction nozzle 4 into the subcutaneous or organic tissue becomes relatively small. Therefore, the suction nozzle 4 can be smoothly inserted and moved forward in the tissue with ease. Besides, since the suction mouth 4b is open aside in the state directed toward the direction different from that of the axis X of the horn 3 or suction nozzle 4, only tissue to be removed can be effectively sucked out through the suction passage 4a.

Figure 4:
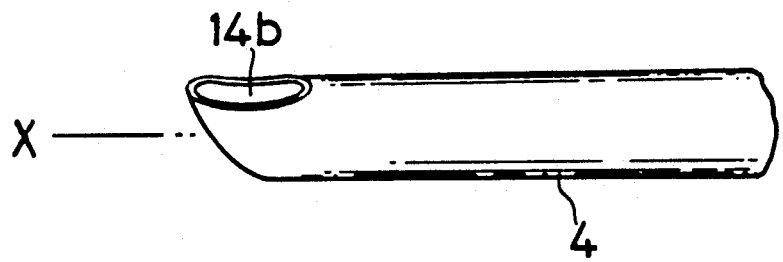
FIG. 4 is a partly enlarged side view of another embodiment of the invention.

Though the suction mouth 4b is formed by cutting aslant the suction nozzle 4 in the aforementioned embodiment, it may be of course formed in various ways so as to satisfy the condition that it opens toward the direction different from that of the axis X of the suction nozzle 4. For instance, as illustrated in FIG. 4, there may be formed a suction mouth 14b in the circumferential side wall of the leading end part of the suction nozzle 4. In this case, the leading end of the suction nozzle 4 may be covered with a slant ellipse plate so as to assume an acute shape.

Figure 5:
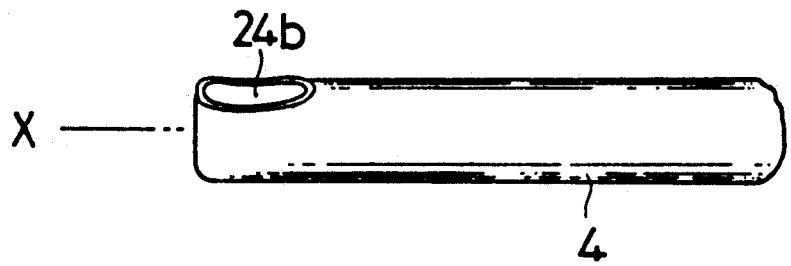
FIG. 5 is a partly enlarged side view of still another embodiment of the invention.
Figure 6:
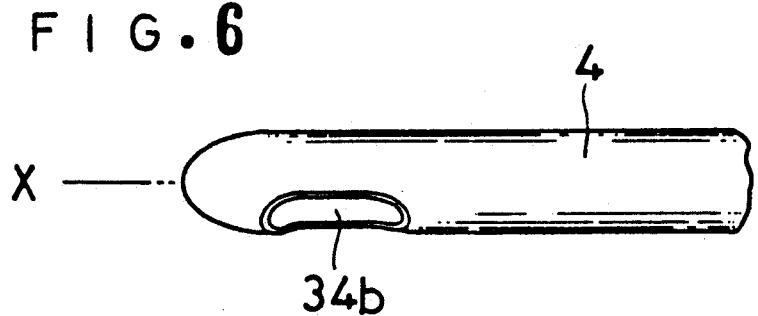
FIG. 6 is a partly enlarged side view of a further embodiment of the invention.

If the resistance produced when advancing the scalpel in the tissue of the living body is disregarded, the leading end of the suction nozzle 4 may be formed perpendicularly to the axis X in a blind state, as illustrated in FIG. 5. To improve the advancing efficiency of the suction nozzle 4 of FIG. 5, which brings about relatively large resistance when advancing in the tissue of the living body, the leading end of the suction nozzle 4 may preferably be formed round as shown in FIG. 6. The suction mouths 24b and 34b formed in the leading end parts 4a of the suction nozzles 4 of the embodiments shown in FIGS. 5 and 6 are open toward the direction different from that of the axis of the respective suction nozzles As is clear from the foregoing disclosure, the ultrasonic surgical scalpel according to this invention enjoys an advantage that the suction nozzle formed on the leading end part of the horn can be stably and smoothly inserted into and moved forward in subcutaneous or organic tissues of a living body without needlessly injuring other tissues such as blood vessels and nerve tissues in advancing the scalpel in under the skin or organic tissues. This effect can be accomplished by forming the suction mouth in the leading end part of the suction nozzle so as to open aside toward the direction different from that of the axis of the suction nozzle. Furthermore, the suction regulating mouth which is provided in the course of the suction pipe connected with the suction nozzle and simple in structure enables the sucking force applied to the suction passage in the suction nozzle to be easily controlled with the finger tip of an operator.

As can be readily appreciated, it is possible to deviate from the above embodiment of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. An ultrasonic surgical scalpel comprising:

handpiece defined by a casing having a rear end and a suction regulating mouth capable of being closed directly with a finger tip;

an ultrasonic vibrator contained within said handpiece, which vibrator generates ultrasonic vibrations when applied with an alternating current;

a horn connected to said vibrator so as to vibrate due to the vibrations generated by the vibrator, which horn comprises a suction nozzle having a leading end and a suction passage axially extending so as to open at the leading end in a non-axial direction of the horn to form a suction mouth;

a flushingpipe provided along an extension surface of said suction nozzle for supplying a solution to around said suction mouth at the leading end of said suction nozzle, said flushing pipe being detachably retained by a joint portion formed on said casing and connected with a conduit through which said solution is fed to said flushingpipe;

an elastic supporting member for supporting said horn at a point substantially one-fourth wavelength of the vibrations generated by said vibrator form a connection point at which said horn and vibrator are connected toe each other; and a connection member mounted where said supporting member is disposed, said connection member having a port connected to said suction passage in said suction nozzle, a port connected to a suction pipe extending outside through said rear ed of said casing, and a port connected to said suction regulating mouth, whereby a suction force is imparted to said suction passage in said suction nozzle through said suction pipe and regulatable by opening or closing said suction regulating mouth with the finger tip so that, when said suction regulating mouth is closed with the finger tip, said suction force in said suction passage is kept normal, and when said suction regulating mouth is open, said suction force in said suction passage is reduced.

2. An ultrasonic surgical a scalpel according to claim 1, wherein said leading end of the suction nozzle is covered with a slant ellipse plate, and said suction nozzle has a circumferential side surface in which said suction mouth is formed.

3. An ultrasonic surgical scalpel according to claim 1, wherein said leading end of the suction nozzle is formed perpendicularly to an axis thereof, and said suction nozzle has a circumferential side surface in which said suction mouth is formed.

4. An ultrasonics surgically scalpel according to claim 1, wherein the leading end of said suction nozzle is in a round shape, and said suction nozzle has a circumferential side surface in which said suction mouth is formed.

5. An ultrasonic surgical scalpel according to claim 1, wherein said suction nozzle has a length substantially three-fourth the wavelength of the vibration generated by said vibrator.

6. An ultrasonic surgical scalpel according to claim 1, further comprising a lid member capable of being detachably fitted in said suction regulating mouth.

7. An ultrasonic surgical scalpel according to claim 1 wherein said suction mouth is formed aslant to an axis of the suction nozzle to form the leading end of the suction nozzle.

* * * * *